(12) United States Patent
Cise et al.

(10) Patent No.: US 6,612,304 B1
(45) Date of Patent: Sep. 2, 2003

(54) RESPIRATORY CARE MULTIPLE ACCESS PORT ASSEMBLY AND ADAPTER

(75) Inventors: David M. Cise, Herriman, UT (US); Edward B. Madsen, Riverton, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 246 days.

(21) Appl. No.: 09/680,125

(22) Filed: Oct. 5, 2000

(51) Int. Cl.[7] .............................................. A61M 16/00

(52) U.S. Cl. ........................... 128/200.26; 128/207.14; 128/912; 604/35

(58) Field of Search ....................... 128/207.16, 207.14, 128/205.19, 200.26, 202.27, 912; 604/158, 163, 190, 251, 252, 264, 268, 523, 533, 534, 535, 537, 35

(56) References Cited

U.S. PATENT DOCUMENTS

| | | |
|---|---|---|
| 274,447 A | 3/1883 | Kennish |
| 2,705,959 A | 4/1955 | Elmore |
| 2,755,060 A | 7/1956 | Twyman |
| 2,912,982 A | 11/1959 | Barsky |
| 3,335,723 A | 8/1967 | Waldman, Jr. |
| 3,444,860 A | 5/1969 | Harrell |
| 3,454,005 A | 7/1969 | Eubanks et al. |
| 3,517,669 A | 6/1970 | Buono et al. |
| 3,614,057 A | 10/1971 | Hospe |
| 3,730,179 A | 5/1973 | Williams |
| 3,757,771 A | 9/1973 | Ruegg et al. |
| 3,774,604 A | 11/1973 | Danielsson |
| 3,794,026 A | 2/1974 | Jacobs |
| 3,825,001 A | 7/1974 | Bennet et al. |
| 3,831,629 A | 8/1974 | Mackal et al. |
| 3,885,561 A | 5/1975 | Cami |
| 3,894,540 A | 7/1975 | Bonner, Jr. |
| 3,902,500 A | 9/1975 | Dryden |
| 3,911,919 A | 10/1975 | Raitto |
| 3,937,220 A | 2/1976 | Coyne |
| 3,991,762 A | 11/1976 | Radford |
| 4,022,219 A | 5/1977 | Basta |
| 4,050,667 A | 9/1977 | Kossett |
| 4,062,363 A | 12/1977 | Bonner, Jr. |
| 4,152,017 A | 5/1979 | Abramson |

(List continued on next page.)

FOREIGN PATENT DOCUMENTS

| | | |
|---|---|---|
| DE | 2920366 A1 | 11/1980 |
| DE | 2939794 A1 | 4/1981 |
| WO | WO 0015276 A | 3/2000 |

OTHER PUBLICATIONS

Hy–Care System Advertisement/Product Information, undated.
Verified Translation of DE 29 20 366 A1, Nov. 19, 2001.
Verified Translation of DE 29 39 794 A1, Nov. 19, 2001.
International Search Report Apr. 12, 2002.

*Primary Examiner*—Weilun Lo
*Assistant Examiner*—Mital Patel
(74) *Attorney, Agent, or Firm*—Dority & Manning (57) ABSTRACT

An assembly provides multiple access ports to an intubated patient's respiratory system through a closed ventilating system. A manifold is configured for attachment to the patient's artificial airway and a conventional ventilating system. A movable adapter is provided at the proximal port of the manifold and includes at least two access ports defined in a movable member. The movable member can be moved into various positions to align any of the access ports with the proximal port of the manifold. Any manner of devices may be mated to the access ports, including devices to ventilate the lungs of the patient with gas or gasses, aspirate secretions from the lungs, oxygenate the lungs, visually inspect selected parts of the respiratory system, sample sputum and gasses, sense parameters such as flow rates, pressure, and temperature, flush the respiratory tract with washing solution, or administer medication, gasses, and/or lavage.

29 Claims, 5 Drawing Sheets

U.S. PATENT DOCUMENTS

| | | |
|---|---|---|
| 4,170,996 A | 10/1979 | Wu |
| 4,193,406 A | 3/1980 | Jinotti |
| 4,214,593 A | 7/1980 | Imbruce et al. |
| 4,235,232 A | 11/1980 | Spaven et al. |
| 4,240,417 A | 12/1980 | Holever |
| 4,256,099 A | 3/1981 | Dryden |
| 4,300,550 A | 11/1981 | Gandi et al. |
| 4,326,520 A | 4/1982 | Alley |
| 4,327,723 A | 5/1982 | Frankhouser |
| 4,327,735 A | 5/1982 | Hampson |
| 4,333,451 A | 6/1982 | Paluch |
| 4,351,328 A | 9/1982 | Bodai |
| 4,387,879 A | 6/1983 | Tauschinski |
| 4,397,442 A | 8/1983 | Larkin |
| 4,440,378 A | 4/1984 | Sullivan |
| 4,454,887 A | 6/1984 | Kruger |
| 4,456,223 A | 6/1984 | Ebling |
| 4,502,482 A | 3/1985 | DeLuccia, deceased et al. |
| 4,510,933 A | 4/1985 | Wendt et al. |
| 4,512,765 A | 4/1985 | Muto |
| 4,534,542 A | 8/1985 | Russo |
| 4,569,344 A | 2/1986 | Palmer |
| 4,607,635 A | 8/1986 | Heyden |
| 4,634,433 A | 1/1987 | Osborne |
| 4,637,389 A | 1/1987 | Heyden |
| 4,638,539 A | 1/1987 | Palmer |
| 4,646,733 A | 3/1987 | Stroh et al. |
| 4,655,752 A | 4/1987 | Honkanen et al. |
| 4,669,463 A | 6/1987 | McConnell |
| 4,696,296 A | 9/1987 | Palmer |
| 4,767,409 A | 8/1988 | Brooks |
| 4,774,945 A | 10/1988 | White et al. |
| 4,805,611 A | 2/1989 | Hodgkins |
| 4,819,664 A | 4/1989 | Nazari |
| 4,821,714 A | 4/1989 | Smelser |
| 4,825,859 A | 5/1989 | Lambert |
| 4,834,726 A | 5/1989 | Lambert |
| 4,836,199 A | 6/1989 | Palmer |
| 4,838,255 A | 6/1989 | Lambert |
| 4,848,331 A | 7/1989 | Northway-Meyer |
| 4,850,350 A | 7/1989 | Jackson |
| 4,872,579 A | 10/1989 | Palmer |
| 4,938,741 A | 7/1990 | Lambert |
| 4,967,743 A | 11/1990 | Lambert |
| 4,969,878 A | 11/1990 | Schmidt et al. |
| 5,025,806 A | 6/1991 | Palmer et al. |
| 5,029,580 A | 7/1991 | Radford et al. |
| 5,031,613 A | 7/1991 | Smith et al. |
| 5,083,561 A | 1/1992 | Russo |
| 5,088,486 A | 2/1992 | Jinotti |
| 5,134,996 A | 8/1992 | Bell |
| 5,140,983 A | 8/1992 | Jinotti |
| 5,176,415 A * | 1/1993 | Choksi .................. 128/202.27 |
| 5,215,522 A | 6/1993 | Page et al. |
| 5,255,676 A * | 10/1993 | Russo .................. 128/205.24 |
| 5,277,177 A | 1/1994 | Page et al. |
| 5,279,549 A | 1/1994 | Ranford |
| 5,346,478 A | 9/1994 | Jinotti |
| 5,354,267 A | 10/1994 | Niermann et al. |
| 5,355,876 A * | 10/1994 | Brodsky et al. ........ 128/202.27 |
| 5,431,157 A | 7/1995 | Mourkidou et al. |
| 5,490,503 A | 2/1996 | Hollister |
| 5,664,564 A | 9/1997 | Palmer |
| 5,694,922 A | 12/1997 | Palmer |
| 5,715,815 A | 2/1998 | Lorenzen et al. |
| 5,735,271 A | 4/1998 | Lorenzen et al. |
| 5,775,325 A * | 7/1998 | Russo .................. 128/202.27 |
| 5,813,402 A | 9/1998 | Jinotti |
| 6,012,451 A | 1/2000 | Palmer |

\* cited by examiner

RESPIRATORY CARE MULTIPLE ACCESS PORT ASSEMBLY AND ADAPTER

FIELD OF THE INVENTION

The present invention relates generally to the field of respiratory care systems for intubated patients.

BACKGROUND

Proper long-term respiratory care of intubated patients requires that a multiple, and often simultaneous, medical procedures be preformed on the patient, including such procedures as, for example, ventilation of the patient's lungs; aspiration of secretions from the lungs; oxygenation of the lungs; elimination or reduction of residual $CO_2$ from the lungs; visual inspection of portions of the respiratory system; sampling sputum and gases; sensing parameters such as flow rates, pressure, and temperature of gases within the respiratory system; and/or the administration of medication, gases, and/or lavage.

An example of when these procedures need to be simultaneously performed is with patients having low lung capacity, such as premature babies and adults suffering from emphysema. In such patients, it is important to remove secretions which have accumulated in the respiratory system without starving the patient for oxygen during the secretion removal process.

Medical care providers thus need a respiratory care assembly to efficiently and safely permit multiple procedures to be performed simultaneously while minimizing stress to the patient.

U.S. Pat. No. 5,735,271 assigned to Ballard Medical Products describes various adapter assemblies which offer significant advancements in the art. When used with a closed ventilating system, such adapter assemblies can provide multiple access to the respiratory system of an intubated patient.

The present invention improves upon the general type of devices described in the '271 patent and further addresses the need in the medical field for improved multiple access assemblies for use with closed ventilating systems.

SUMMARY OF THE INVENTION

Objects and advantages of the invention will be set forth in part in the following description, or may be obvious from the description, or may be learned through practice of the invention.

The present invention is directed to a respiratory care assembly for use with a closed ventilating system, the assembly providing a plurality of access pathways or ports to a patient's artificial airway thus allowing uninterrupted flow of ventilating gases to the patient during additional procedures.

The assembly of the present invention includes a manifold for interfacing with the patient's artificial airway, for example a tracheostomy tube, placed in the patient's respiratory tract. As used herein, the phrase "artificial airway" includes devices such as tracheostomy tubes, endotracheal tubes, and the like that keep the patient's natural airway open so that adequate lung ventilation can be maintained. The manifold has a distal port for connecting to the patient's artificial airway, and a ventilator port for connection to a ventilator to at least partially assist an intubated patient in respiration. The manifold further includes a proximal port that provides access through the manifold to the distal port.

A multi-port adapter is mounted on the manifold in communication with the proximal port and is movable to various operating positions. For example, the adapter may include a movable rotor member that is rotatably mounted to a stationary stator member. The stator member contains an opening or access to the proximal port. The movable component of the adapter includes at least a first and a second access port defined therethrough. The movable component, for example the rotor member, is movable between at least first and second positions such that in the first position the first access port is in axial alignment and fluid communication with the proximal port and the second access port is out of alignment with the proximal port, and in the second position the second access port is in axial alignment and fluid communication with the proximal port and the first access port is out of alignment with the proximal port. The movable member may also be movable to a third position wherein both of the access ports are misaligned or isolated from the proximal port.

The access ports are configured for receipt of any manner of conventional catheter assemblies, cartridges, or similar conduits. These catheter assemblies or cartridges may be releasably connected to the access ports. At least one catheter may be a suction catheter device that includes an inner catheter tube.

The adapter may be moved or rotated such that the access port (i.e., the first access port) mated with the suction catheter assembly is brought into axial alignment with the proximal port of the manifold. The catheter tube within the suction catheter assembly is advanced through the first access port, through the proximal port of the manifold, and ultimately into the patient to allow the suctioning of secretions as described herein. After the catheter tube is retracted, the adapter is rotated such that the first access port is moved out of axial alignment with the proximal port of the manifold.

Similarly, the second access port mated with a second type of catheter assembly may be rotated into axial alignment with the proximal port of the manifold. The second catheter assembly may be, for example, an oxygen supply catheter cartridge having an inner tube for providing additional oxygen to the patient. It should be appreciated that the assembly is not limited to any particular catheter device, and the access ports can be configured to accommodate any type of catheter assembly or cartridge for carrying out a desired procedure through the patient's airway.

According to one aspect of the invention, the ventilator port may be disposed at an angle such that an axis of the ventilator port is at an angle of more than about 90°, preferably about 120°, with respect to an axis of the distal port. This angle allows for better (i.e. more efficient, lower pressure drop) ventilation to the intubated patient and reduces stress on the patient.

According to another aspect of the invention, at least one channel may be formed between at least two of the access ports provided on the movable member of the adapter to place the channels in fluid communication. This configuration allows a relatively small partial flow of air or other fluid between each of the access ports connected by the channel during a suction cleaning operation. It has been found that this flow allows for complete fluid evacuation of the suction catheter or other device during a suction cleaning operation. Furthermore, this flow results in a turbulent flow around the catheter being cleaned, such flow significantly improving the cleaning operation, particularly a lavage cleaning operation of a suction catheter.

For example, a suction catheter assembly mated with the first access port may be in communication with a lavage port provided at the distal end of the suction catheter or formed directly on the first access port. Once the catheter tube has been withdrawn from the patient, it must be cleaned of secretions and mucus. Typically, the cleaning procedure occurs once the clinician has rotated the adapter such that neither the first access port nor the second access port is in axial alignment with the proximal port of the manifold. A lavage solution is introduced through the lavage port and into a distal fitting of the catheter assembly for cleaning the distal tip of the catheter tube during retraction of the catheter tube. In this configuration, the catheter tube will suction the lavage solution from the catheter assembly, carrying at least some of the mucus or secretions that have collected thereon. The cleaning operation occurring in the first access port will cause air or fluid to be sucked through the channel between the first access port and the second access port. This introduction of air or fluid creates greater turbulence about the distal tip of the catheter and aids in the cleaning process of the catheter.

It is important to note that additional access ports may be formed within the movable component of the adapter to allow the connection of additional catheters, conduits, or similar devices to the adapter. In one configuration, for example, four catheters may be connected at four access ports formed in the adapter.

Additionally, according to another aspect of the invention, a seal or gasket may be disposed between the movable and stationary components of the multi-port adapter. A gasket, such as a friction-fit gasket, may be disposed between these components to insure seal integrity and ease of manipulation of the components during operation. The ease of manipulation also provides greater comfort to the patient connected to the manifold.

Moreover, the inclusion of swivels or similar tension reducing devices on some or all of the ports of the manifold may be desired to reduce the torsional effect of twisting of any or all catheters, tubes, other devices connected to the manifold and adapter. The ability to relieve twisting stresses provides greater comfort to the patient and aids in the manipulation of the manifold and adapter assembly.

It may also be desired to provide a grip enhancing surface on the movable component of the adapter. For example, in the embodiment wherein the adapter includes a rotor member rotatably mounted on a stator member, a grip enhancing ring member may be provided on the circumference of the rotor member. The "grip enhancements" may comprise protrusions, recesses, etc. formed on the ring. This feature enhances the clinician's ability to rotate the rotor member with respect to the stator member and thus reduces the possible stresses that may be inflicted on the intubated patient connected to the manifold.

DETAILED DESCRIPTION OF PREFERRED EMBODIMENT

Reference is now made in detail to one or more embodiments of the invention, examples of which are shown in the drawings. Each example is provided as a means of explaining the invention, and not as a limitation of the invention. For example, features illustrated or described as part of one embodiment may be used on another embodiment to yield still a further embodiment. It is intended that the present invention include modifications and variations to the embodiments described herein.

In the drawings, each embodiment is arranged such that the distal direction (referring generally to the direction of the patient) is located at the bottom of the figure while the proximal direction (generally referring to the direction of the clinician) is located at the top of the figure.

As mentioned, the present invention relates generally to the type of devices described in U.S. Pat. No. 5,735,271 assigned to Ballard Medical Products. The '271 patent is incorporated herein in its entirety for all purposes.

An embodiment of a respiratory care assembly according to the present invention is illustrated generally as 100 in the figures. The assembly 100 provides multiple access pathways or ports to a patient's artificial airway through which any number of various procedures may be performed without interrupting or disconnecting the patient from the ventilation system. With reference to the figures in general, the assembly 100 includes a manifold 101 and a movable adapter component 102. The manifold 101 includes a distal port 103 configured for connecting the assembly 100 to a patient's artificial airway, such as an endotracheal tube. The manifold 101 includes a ventilator port 104 configured for connecting the assembly 100 to any manner of conventional ventilation system or assisted breathing device. A proximal port 105 is also provided and will be discussed in greater detail herein.

Figure 3:
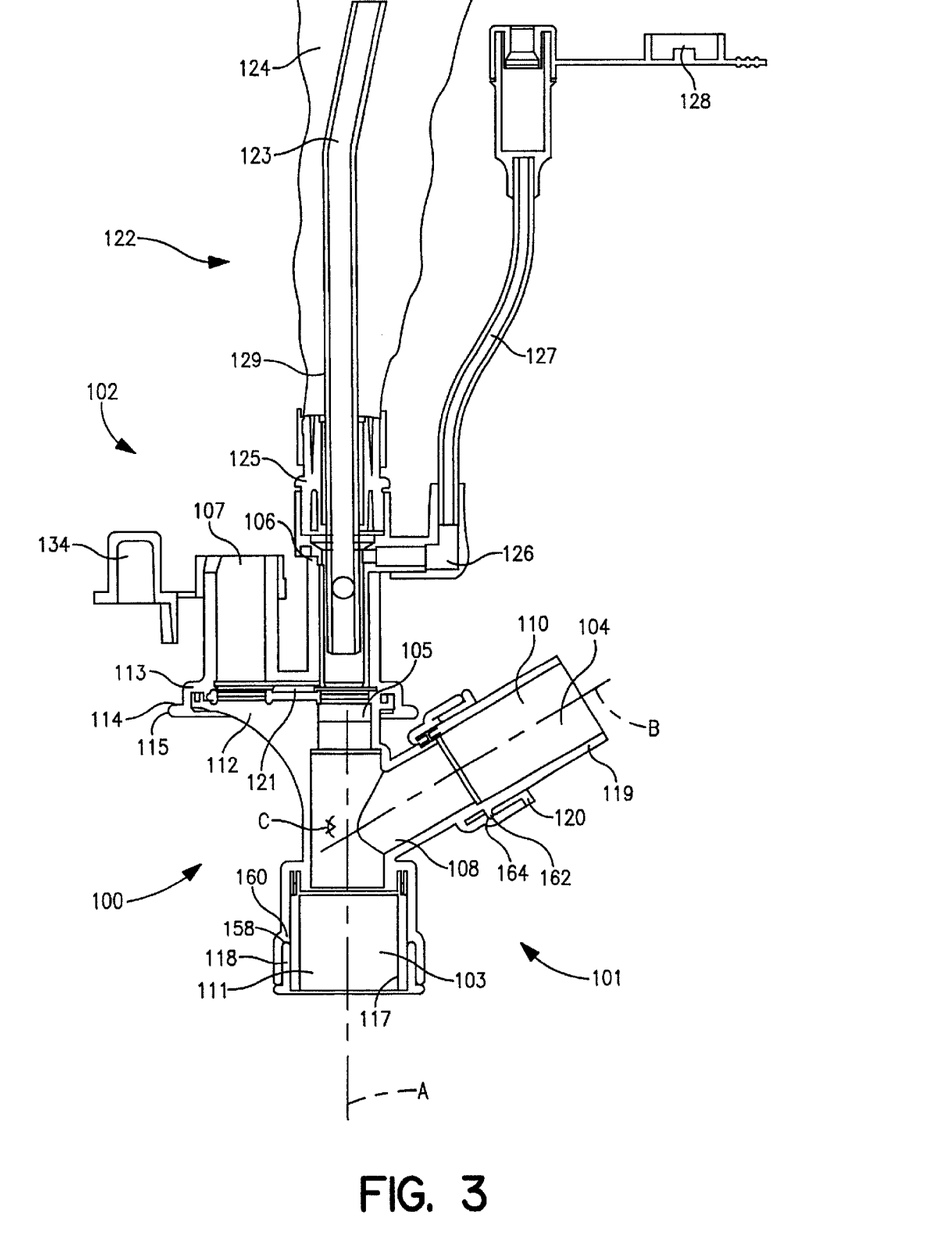
FIG. 3 is a cross-sectional plan view of an embodiment of the present invention taken along a longitudinal centerline of the device shown in FIG. 2.

The manifold 101 defines an internal channel or passage 111 therethrough from the proximal port 105 to the distal port 103 along a longitudinal axis A (FIG. 3). The ventilator port 104 is also in communication with the internal channel 111 through an elbow fitting 108. The elbow fitting 108 includes a cylindrical wall 109 defining a hollow interior 110 having an axis B (FIG. 3), into which ventilating gases are delivered from a suitable commercially available ventilator that is attached to the ventilator port 104. The elbow 108 may be formed with the manifold 101 as one piece from a suitable synthetic resinous material, or may be assembled from independent components.

The ventilator port 104 may be disposed with respect to the distal port 103 so that the angle C between the longitudinal axis A of the distal port 103 and axis B of the ventilator port 104 is greater than 90 degrees. For example, in the embodiment of FIG. 3, the angle C is about 120 degrees. It has been shown that this angular relationship between the ventilator port 104 and the distal port 103 significantly reduces resistance to air flow to and from the ventilator. It has been found that air flow resistance decreases as the angle between the ventilator port 104 and the distal port 103 increases. Applicants have found that an angle of about 120 degrees is useful, although other angles greater than 90 degrees may also be used.

It may be desired to provide swivel connections at the ventilator port 104 and the distal port 103. Such swivels allow devices, conduits, and the like that are attached to the manifold 101 to rotate relative to the manifold. This reduces torsional and twisting effects which can cause patient discomfort, while providing greater flexibility and freedom of movement to these attachments during manipulation by the clinician and movement by the patient. Embodiments of suitable swivel connections are shown in the figures. For example, referring to the distal port 103, a cylindrical swivel collar 117 having a circumferential ring 158 is rotatably disposed in the distal port 103. The ring 158 abuts against a shoulder 160 formed in the distal port housing. The swivel collar 117 is held in position by a retaining collar 118 press-fitted into the distal port 103, as particularly seen in FIG. 3. This type of configuration may be desired because it does not require chemical bonding or adhesive bonding of the components. Likewise, referring to the ventilator port 104, a cylindrical swivel extension 119 may be provided with a circumferential ring 162. The ring 162 abuts against the shoulder 164 formed in the manifold 101. The swivel extension 119 is rotatably disposed within the ventilator port 104 and held in position by a press-fitted retaining collar 120 (FIG. 3). The ports 103 and 104 may include bell-shaped housings, as shown in the figures, having stepped annular walls defining the shoulders 160 and 164 to accommodate the swivels 117 and 119, respectively. However, it should be appreciated that various shapes and engaging structure between the swivels and ports may be utilized in this regard.

It should also be appreciated by those skilled in the art that various configurations of swivelling or rotating members other than the collar configurations shown in the figures may be utilized to provided a "swivel" capability at the respective ports 103 and 104.

Although not illustrated in the figures, it should be appreciated that suitable swivel connections could also be provided at the distal ends of the tubes, catheters, connections, or any other device mated with the respective ports 103 and 104. In other words, the 'swivel capability may be provided by the device to be attached to the manifold 101.

The assembly 100 also includes an adapter 102 with multiple access ports. The adapter 102 includes a component that is movably mounted on a stationary supporting component, the supporting component being attached or formed on the manifold 101. In the illustrated embodiments, the movable component of the adapter 102 is rotatably mounted relative to the manifold 101, as will be described in greater detail below. It should be appreciated, however, that the rotatable adapter configuration described herein is only an example of a suitable "movable" configuration. For example, the adapter could comprise a component that slides linearly relative to the manifold 101.

In the "rotatable" embodiment of the adapter shown in the figures, the stationary component of the adapter is a stationary stator member 112 formed at the proximal port 105 of the manifold 101. The stator member 112 may be formed as an integral portion of the manifold 101, or may be separately formed and attached thereto. As shown particularly in FIG. 1, the stator member 112 defines the inlet to the proximal port 105 through an opening 166. The stator member 112 may be formed as a generally cylindrical plate 170 with a uniform thickness about its outer circumference.

Figure 1:
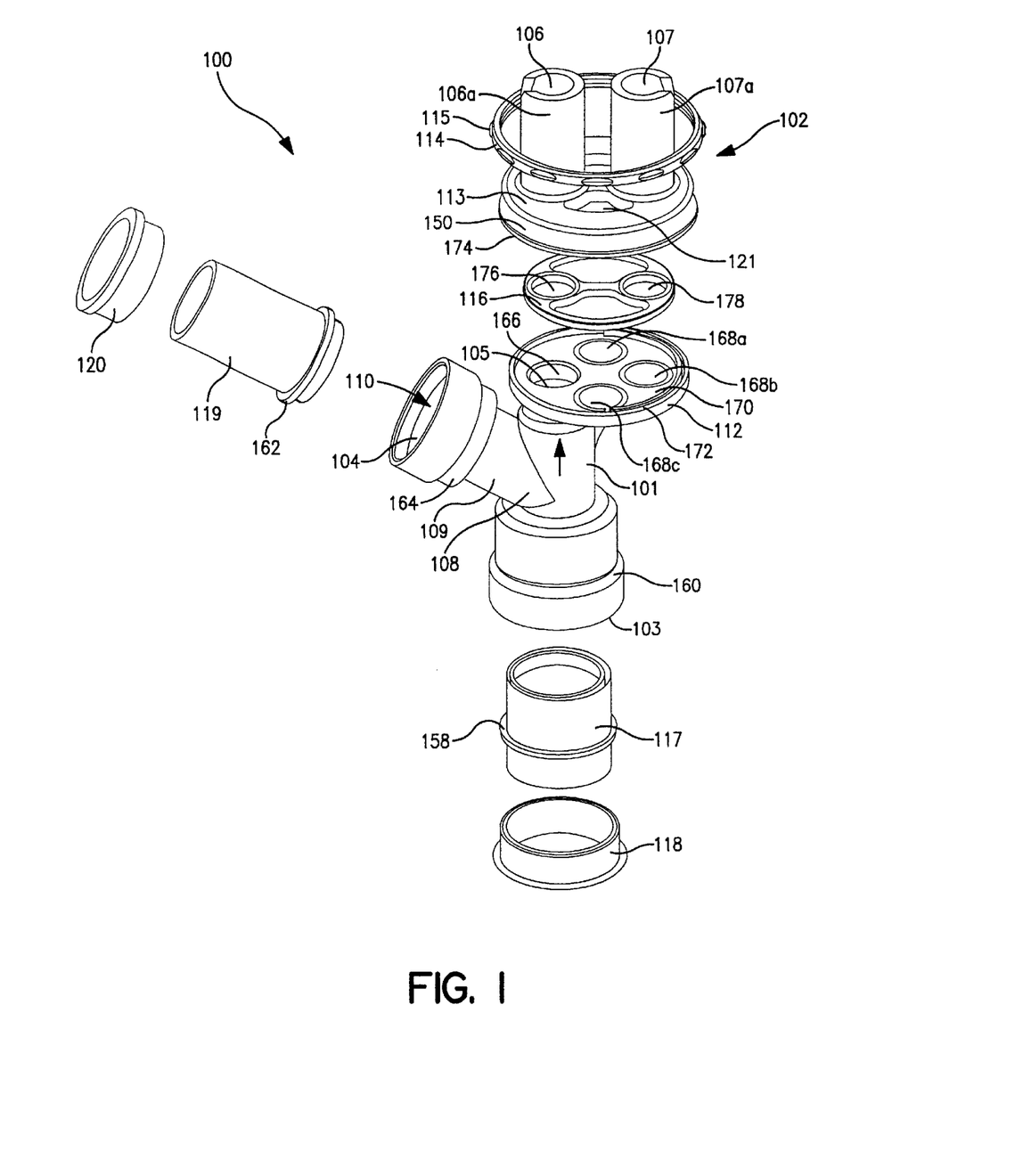
FIG. 1 is a perspective exploded view of an embodiment of the present invention.

The movable component of the adapter 102 includes a rotor member 113 having the first access port 106 and the second access port 107. As shown in FIG. 1, the openings of the access ports 106 and 107 are disposed at the upper portion of cylindrical columns 106a and 107a. The rotor member 113 is formed so that it rotatably engages stator member 112. For example, the rotor member 113 includes a circumferential wall 150 having an outwardly extending ring 174 that rotationally engages within a groove or race of a circumferential lip 172 which extends upwardly from the stator member 112. The rotor member 113 snaps onto the stator member 112 without bonding or adhesives.

As shown in the illustrated embodiments, the adapter 102 includes access ports 106 and 107, although additional access ports may also be provided. Each of these ports are defined on the movable rotor member 113 and may be selectively brought into alignment, and thus in fluid communication, with the proximal port 105. For example, the rotor member 113 is rotatable between first and second positions such that in the first position, the first access port 106 is in axial alignment and fluid communication with the proximal port 105 and the second access port 107 is out of alignment with the proximal port 105. In the second position, the second access port 107 is in axial alignment and fluid communication with the proximal port 105 and the first access port is out of alignment with the proximal port 105. The rotor member 113 may also be moved to a third position wherein neither of the ports 106 and 107 are in alignment with the proximal port 105 for reasons discussed further on.

Various indexing features may be provided so that, as the rotor member 113 is rotated with respect to the stator member 112, the clinician is provided with an indication, such as, for example, an increased resistance to rotation, an audible click or the like, that the rotor member 113 has been rotated to the desired position. In the embodiment depicted in FIG. 1, raised rings 168a–168c are positioned on the stator member plate 170. These raised rings are configured to engage distally projecting features on the rotor member 113, such as projections of the cylindrical columns 106a and 107a. The raised rings are positioned so that, as the rotor member 113 is rotated with respect to the stator member 112, an increased resistance or "click" is created when the columns 106a and 107a move over and "nest" in the raised rings.

A seal 116 may also be disposed between the rotor member 113 and the stator member 112 to ensure an adequate seal between the components to maintain the integrity of the ventilation system. In a particular embodiment, the seal 116 is a gasket seal having openings 176 and 178 formed therein. The openings 176 and 178 may correspond to the first and second access ports 106 and 107. The portion of the seal 116 defining the openings 176 and 178 may constitute the "projections" of the columns 106a and 107a that ride over the raised rings 168a–168c, as described above. The seal 116 may be formed of any variety of materials, such as, for example, a silicon rubber, thermoplastic elastomer, or other similar polymer. In selected embodiments, the seal 116 does not require bonding or adhesives, but rather is held frictionally against the underside surface of the rotor member 113 by being press-fitted against the circumferential wall 150 of the rotor member 113. The seal 116 may also be bonded in place by heat, adhesive, or sonic welds.

A grip enhancing surface may be provided on the circumferential rim of the rotor member 113 to aid the clinician in rotating the rotor member 113 between its various operative positions. In the illustrated embodiments, a grip ring 114 is provided for this purpose. The grip ring 114 is formed such that it can be pressed onto the wall 150 of the rotor member 113. To further enhance ease of use, the ring 114 may include a plurality of radially extending protrusions 115 disposed circumferentially about the ring 114.

Figure 4:
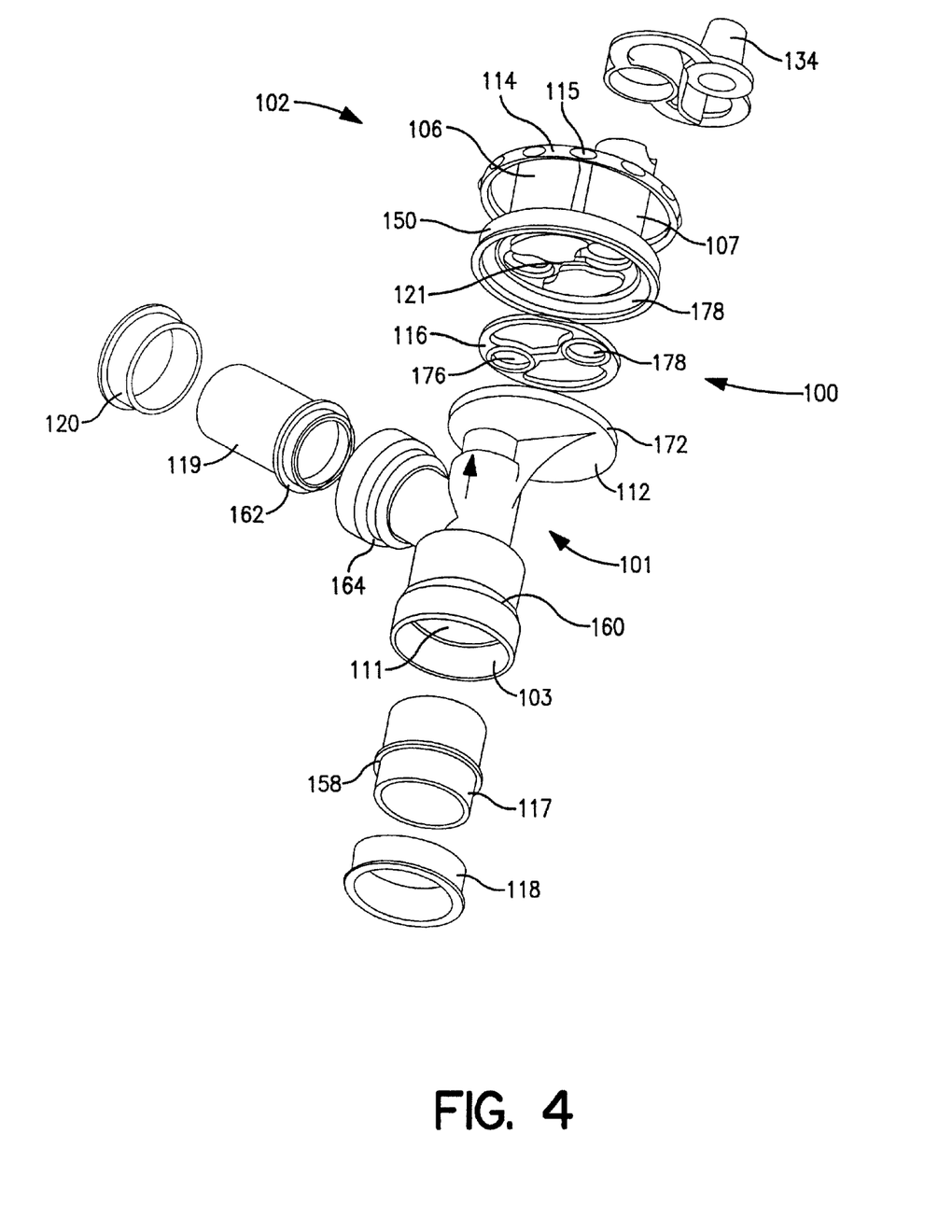
FIG. 4 is an exploded assembly view of an embodiment of the present invention.

As shown in FIG. 4, a channel 121 may be formed in the rotor member 113 between the access ports 106 and 107 so that the ports are in fluid communication with each other. In the illustrated embodiments, the channel is a straight conduit molded into the rotor member 113 between the distal ends of the access port columns 106a and 107a.

Each of the access ports defined in the rotor member 112 may be provided with plugs to close the access ports when they are not in use. As shown in the figures, plug devices 134 may be attached to at least one of the cylindrical columns 106a or 107a to help assure that the plug remains easily accessible to the clinician. The plug may also permit the ports to be isolated when there is no device, such as a catheter, inserted into the respective port.

Figure 2:
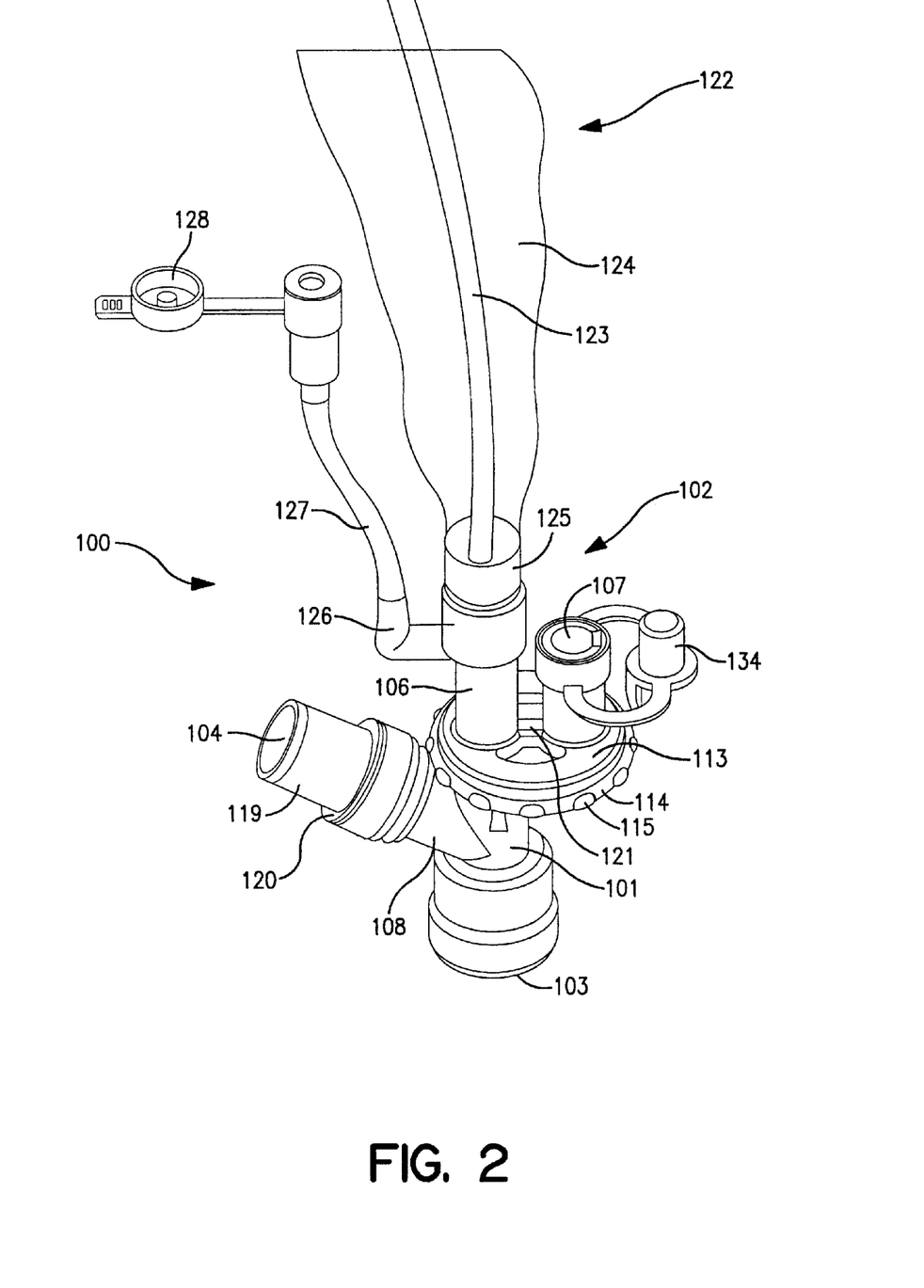
FIG. 2 is a perspective view of an embodiment of the present invention.
Figure 5:
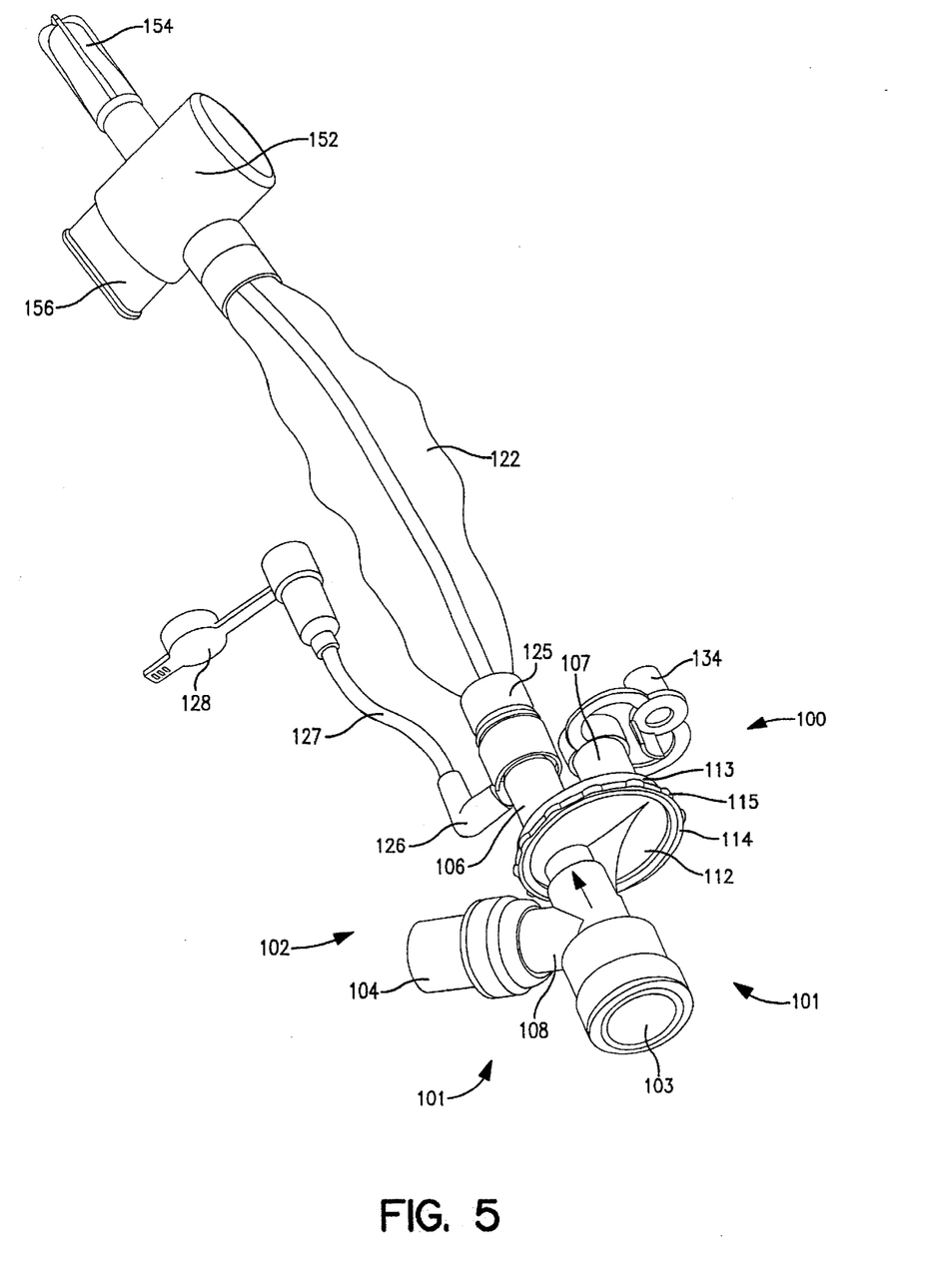
FIG. 5 is an alternate perspective view of an assembly according to the present invention.

Operational principles of the assembly 100 will now be discussed in order to further explain the invention. Referring to FIGS. 2, 3, and 5, a catheter assembly or cartridge 122 has been inserted into the first access port 106. While the catheter assembly 122 is removably attached to the access port 106, it may remain attached to the port 106 until it is replaced with a new catheter assembly 122. The catheter assembly 122 depicted in the figures is a suction catheter assembly, although it should be understood that a variety of catheter assemblies or cartridges may be attached to either of the access ports 106 and 107. The illustrated suction catheter assembly 122 is known to those skilled in the art and is described, for example, in U.S. Pat. No. 5,735,271 incorporated herein by reference. Briefly, the catheter assembly 122 includes a catheter tube 123 surrounded by a sleeve or sheath 124. The distal end of the sleeve is fitted into a fitting 125. The fitting 125 is removably connectable to the first access port 106 so that the catheter 122 may be easily removed from the first access port 106 if desired.

To perform a suctioning procedure, the clinician grips the ring 114 and rotates the rotor member 113 to a first position so that the first access port 106 is aligned with the proximal port 105. In this position, the catheter tube 123 may slide within the catheter assembly 122 and advances through the first access port 106, through the manifold 101 and the distal port 103, and into the patient through the artificial airway. Mucus and other secretions can then be suctioned out through the catheter tube 123.

Once suctioning of the mucus and secretions has been completed, or retraction for another reason is desired, the catheter tube 123 is withdrawn by the clinician through the artificial airway, the manifold 101, the adapter 102, and back into the catheter 122. While a portion of the mucus and secretions that have accumulated on the catheter tube 123 are removed as the suction tube is withdrawn through the fitting 125, the catheter tube 123 must be cleaned further in a lavage cleaning operation. A lavage port 126 is provided in fluid communication with the first access port 106. The lavage port 126 may be formed as a component of the access port 106 or, as shown in the figures, may be provided at the distal end of the suction catheter 122. Those skilled in the art will recognize that a similar lavage port may be disposed or formed on any access port of adapter 102. The lavage port 126 provides a conduit between the interior of the first access port 106 and a lavage tube 127 connected to the lavage port 126 and connectable to a source of lavage solution. The lavage tube 127 is shown with a removable cap 128 such that the lavage tube 127 may be plugged when it is not in use.

The catheter assembly 122 may be connected to a suction valve 152 at its proximal-most end via an appropriate fitting 154. The suction valve 152 may be a push button activated device 156 or a similar actuator. A suitable suction catheter utilizing a push button actuator is available from Ballard Medical Products and is known to those skilled in the art.

With this configuration, a clinician may selectively suction the patient's lungs and clean the suction catheter without disconnecting or interrupting the ventilation system by aligning the suction catheter with the proximal port 105 through the access port 106 and thereafter actuating the suction catheter, for example by actuating valve 152 via actuator 156.

The lavage cleaning procedure occurs typically as the catheter tube 123 is retracted into catheter assembly 122 after the suction procedure has been completed. The lavage solution breaks down and removes mucus and secretions that may have collected on the exterior surface of the catheter tube 123. As suction is maintained through suction tube 123 during the cleaning procedure, the lavage solution is effectively suctioned from the assembly 100.

It is envisioned that any other type of catheter assembly or cartridge may be mated to the second access port 107, including an oxygenation catheter cartridge that allows for connection of an oxygen source without the introduction of ambient air into the adapter. This configuration provides the greatest protection to the patient. A press-fit arrangement with the second access port 107 would allow for the rapid connection and disconnection of the oxygenation catheter cartridge during manipulation. Moreover, though the present invention has been described with the inclusion of a suction catheter, those skilled in the art will recognize that additional access ports or the referenced access ports may provide a location for the connection of oxygen sources, medication sources, or the inclusion of sensors capable of sensing parameters such as flow rates, pressures, temperatures, or similar properties. The connection of a flushing device allows for the inundation of liquid, if necessary. Those skilled in the art will recognize that virtually any number of access ports may be formed in the device to accommodate any manner of connector, supply tube, catheter assembly, catheter cartridge, and the like.

As described earlier, a channel 121 is defined between this first access port 106 and an additional access port, such as the second access port 107. The channel may have a variety of cross-sectional shapes so long as a channel or conduit is defined between the ports that provides at least a minimal amount of fluid flow between the ports. With this configuration, additional air or gas may be drawn into the first access port 106 from the access port 107 through the channel 121 during cleaning of the catheter tube 123. It has been shown that this additional air provides additional turbulence during the cleaning of the exterior surface of inner suction tube 123. This turbulence results in a vigorous cleaning of the exterior surface 129 of the suction tube 123 by the lavage solution. If the second access port 107 is not connected to a gas source, the additional air may be ambient air drawn through the access port 107 simply by removing plug 134 from the access port 107. Oxygen or another gas may also be supplied to access port 107 by a suitable supply tube or catheter connected thereto. This oxygen or other gas can also serve as the additional turbulent flow through channel 121.

Other notable features of the invention include the formation of some or all of the components out of clear or translucent materials such that visual inspection of the components is possible. This also allows the clinician to monitor the color and consistency of the mucus and secretions, and more carefully monitor the cleaning of the catheter.

The components described herein may be formed of a variety of materials and from a variety of manufacturing processes. In some embodiments, the components of the present invention may be injection molded from a medical grade synthetic resinous material such as acrylic, flexible PVC's, modified polypropylene, or similar substances.

What is claimed is:

1. A respiratory care assembly for providing a plurality of access ports to a patient's artificial airway, said assembly comprising:
   a manifold having
      a distal port configured for connecting directly to an artificial airway;
      a ventilation port configured for connecting to a ventilator, said ventilation port disposed so that a longitudinal axis of said ventilation port is at an angle greater than 90 degrees relative to a longitudinal axis of said distal port;
      a proximal port providing access through said manifold to said distal port;
      an adapter having an adapter component rotatably mounted on said manifold at said proximal port, said adapter component further comprising at least a first and a second access port defined therethrough; and
      wherein said rotatable adapter component is rotatable between first and second positions such that in said first position said first access port is in axial alignment and fluid communication with said proximal port and said second access port is out of alignment with said proximal port, and in said second position said second access port is in axial alignment and fluid communication with said proximal port and said first access port is out of alignment with said proximal port and a surgical instrument is prevented from being inserted through said first access port and into said distal port when said rotatable adapter is in said second position; and
      a channel defined in said rotatable adapter component between said first and second access ports such that said first and second access ports are in fluid communication with each other.

2. The assembly as in claim 1, wherein said rotatable adapter component is rotatable to a third position wherein neither of said first nor second access ports are in axial alignment with said proximal port.

3. The assembly as in claim 1, wherein said adapter further comprises a stator member having a stator plate, said stator member configured on said manifold at said proximal port and defining an access through said proximal port, said rotatable adapter component comprising a rotor member rotatably mounted to said stator plate, said first and second access ports defined in said rotor member.

4. The assembly as in claim 3, further comprising a seal between said rotor member and said stator member.

5. The assembly as in claim 4, wherein said seal is a friction-fit gasket seal.

6. The assembly as in claim 3, further comprising a grip enhancing surface defined on an outer circumferential surface of said rotor member.

7. The assembly as in claim 6, wherein said grip enhancing surface comprises a grip ring mounted on said rotor member, said grip ring further comprising a plurality of radially extending protrusions.

8. The assembly as in claim 1, wherein at least one of said ventilation port and said distal port comprise a swivel connector mated therewith.

9. The assembly as in claim 1, further comprising a first catheter removably connected to one of said first and second access ports.

10. The assembly as in claim 1, further comprising a catheter connected to each of said first and second access ports.

11. The assembly as in claim 1, further comprising a suction catheter connected to said first access port, said suction catheter having a suction tube movable through said adapter and said manifold into the patient's artificial airway.

12. The assembly as in claim 11, further comprising a lavage port in communication with said first access port.

13. The assembly as in claim 11, wherein said lavage port is configured on said access port.

14. The assembly as in claim 11, wherein said lavage port is configured on said suction catheter.

15. The assembly as in claim 11, further comprising a channel defined in said adapter between said first and second access ports such that during a lavage operation air is drawn from said second access port through said channel and into said first access port.

16. A respiratory care assembly for providing multiple accesses to a patient's artificial airway, said assembly comprising:
   a manifold having a distal port configured for connecting directly to an artificial airway, and a ventilation port configured for connecting to a ventilator;
   said manifold further comprising a proximal port providing access through said manifold to said distal port;
   an adapter movably mounted on said manifold at said proximal port, said adapter further comprising at least a first access port and a second access port defined therethrough, said adapter movable between first and second positions such that in said first position said first access port is in axial alignment and fluid communication with said proximal port and said second access port is out of alignment with said proximal port, and in said second position said second access port is in axial alignment and fluid communication with said proximal port and said first access port is out of alignment with said proximal port;
   a suction catheter connectable to said first access port, said suction catheter having a suction tube movable through said adapter and said manifold into the patient's artificial airway when said adapter is in said first position and blocked from moving through said adapter and said manifold when in said second position; and
   a channel defined in said adapter between said first and second access ports such that during a lavage cleaning operation of said suction catheter, air is drawn from said second access port through said channel and into said first access port.

17. The assembly as in claim 16, wherein said ventilation port is disposed so that a longitudinal axis of said ventilation port is at an angle greater than 90 degrees relative to a longitudinal axis of said distal port.

18. The assembly as in claim 16, wherein said adapter is rotatably mounted on said manifold.

19. The assembly as in claim 18, wherein said adapter is rotatable to a third position wherein neither of said first nor second access ports are in axial alignment with said proximal port.

20. The assembly as in claim 19, wherein said adapter comprises a stator member having a stator plate, said stator member configured on said manifold at said proximal port and defining an access through said proximal port, and a rotor member rotatably mounted to said stator plate, said first and second access ports defined in said rotor member.

21. The assembly as in claim 20, further comprising a seal between said rotor member and said stator member.

22. The assembly as in claim 21, wherein said seal is a friction-fit gasket seal.

23. The assembly as in claim 20, further comprising a grip enhancing surface defined on an outer circumferential surface of said rotor member.

24. The assembly as in claim 23, wherein said grip enhancing surface comprises a grip ring mounted on said rotor member, said grip ring further comprising a plurality of radially extending protrusions.

25. The assembly as in claim 16, wherein at least one of said ventilation port and said distal port comprise a swivel connector mated therewith.

26. The assembly as in claim 16, further comprising an additional catheter connectable to said second access port for performing an additional medical procedure through said manifold.

27. The assembly as in claim 16, further comprising a lavage port in communication with said first access port.

28. The assembly as in claim 27, wherein said lavage port is configured on said access port.

29. The assembly as in claim 27, wherein said lavage port is configured on said suction catheter.

\* \* \* \* \*